(12) United States Patent
Forgacs

(10) Patent No.: US 7,675,298 B2
(45) Date of Patent: Mar. 9, 2010

(54) DETERMINING FLUID CHARACTERISTICS

(75) Inventor: Peter Forgacs, Jerusalem (IL)

(73) Assignee: Hewlett-Packard Development Company, L.P., Houston, TX (US)

( * ) Notice: Subject to any disclaimer, the term of this patent is extended or adjusted under 35 U.S.C. 154(b) by 265 days.

(21) Appl. No.: 11/764,059

(22) Filed: Jun. 15, 2007

(65) Prior Publication Data
US 2008/0309316 A1 Dec. 18, 2008

(51) Int. Cl.
G01R 27/08 (2006.01)
G01N 27/00 (2006.01)
G01N 27/02 (2006.01)

(52) U.S. Cl. .......................... 324/713; 324/71.1; 324/444

(58) Field of Classification Search ................. 324/71.1, 324/713, 444
See application file for complete search history.

(56) References Cited

U.S. PATENT DOCUMENTS

| | | | |
|---|---|---|---|
| 4,010,715 A | | 3/1977 | Robar et al. |
| 4,333,083 A | | 6/1982 | Aldridge |
| 4,626,786 A | | 12/1986 | Bodecker et al. |
| 5,046,416 A | | 9/1991 | Freyer et al. |
| 5,570,193 A | | 10/1996 | Landa et al. |
| 5,576,617 A | | 11/1996 | Webb et al. |
| 5,793,490 A | | 8/1998 | Forgacs et al. |
| 6,128,450 A | * | 10/2000 | Suetsugu ................ 399/58 |
| 6,154,620 A | | 11/2000 | Hagiwara |
| 6,386,683 B1 | * | 5/2002 | Muroi et al. ............ 347/55 |
| 6,562,539 B1 | | 5/2003 | Chatow et al. |
| 6,596,068 B1 | | 7/2003 | Ito et al. |
| 6,979,481 B2 | | 12/2005 | Gaynor et al. |
| 7,172,651 B2 | | 2/2007 | Chen et al. |
| 2004/0033323 A1 | | 2/2004 | Gaynor et al. |
| 2004/0255820 A1 | | 12/2004 | Chen et al. |
| 2005/0141910 A1 | | 6/2005 | Hsin |
| 2006/0027137 A1 | | 2/2006 | Smith |
| 2006/0076249 A1 | | 4/2006 | Meisegeier et al. |

FOREIGN PATENT DOCUMENTS

| | | |
|---|---|---|
| JP | 06-027069 | 4/1994 |
| JP | 2006-214975 | 8/2006 |

OTHER PUBLICATIONS

Conductivity Guide, Van London pHoenix Co., Houston, Texas, reprinted from the Internet at http://www.v1-pc.com/conductivityguide.html, 2007, 7 pgs.

* cited by examiner

*Primary Examiner*—Amy He

(57) ABSTRACT

Characteristics of a fluid are determined, in one embodiment, by flowing the fluid (which may contain charged particles) between a plurality of electrode pairs, applying respective DC voltages across at least two of the electrode pairs, and measuring resulting currents through the fluid at the respective electrode pairs. In one example, respective plates of the electrode pairs are configured so that they do not fully encircle one another.

19 Claims, 9 Drawing Sheets

DETERMINING FLUID CHARACTERISTICS

BACKGROUND

Many factors contribute to the quality of a printing process. It can be appreciated that there is an ongoing desire to improve the quality of the print jobs. Therefore, monitoring one or more characteristics associated with a printing process may be desirable as this may promote higher quality print jobs. Nevertheless, monitoring certain characteristics may be difficult, such as one or more characteristics associated with a static pool of ink of a printing press, for example.

Various ink parameters strongly influence the performance of the press regarding print quality, operational stability and life time of consumables, therefore measuring and controlling such ink characteristics may be desirable.

BRIEF DESCRIPTION OF THE DRAWINGS

To the accomplishment of the foregoing and related ends, the following description and annexed drawings set forth in detail certain illustrative aspects and/or embodiments of the disclosure. These are indicative of but a few of the various ways in which one or more aspects and/or embodiments of the disclosure herein may be employed. Other aspects, advantages and/or novel features of the disclosure will become apparent from the following detailed description when considered in conjunction with the annexed drawings.

DETAILED DESCRIPTION

Figure 1:
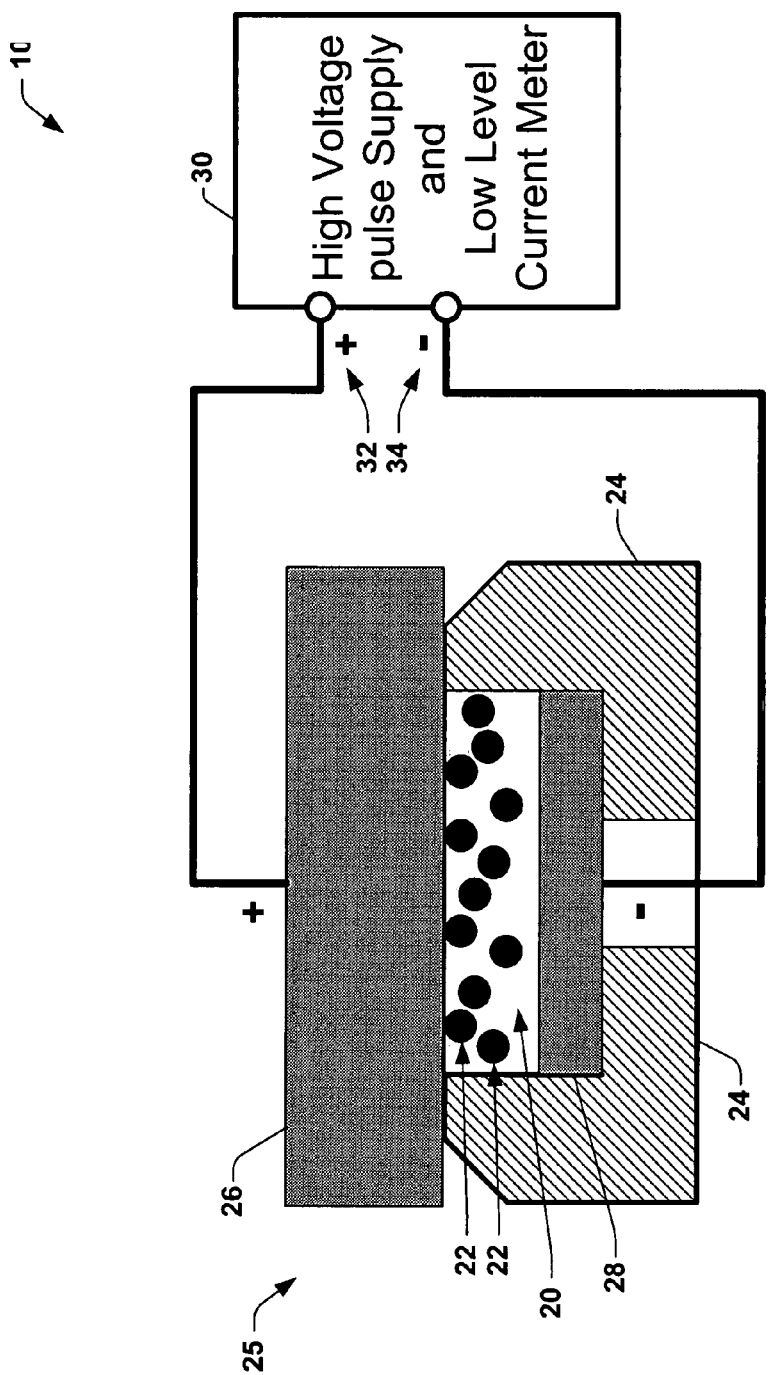
FIG. 1 is a functional schematic diagram of a laboratory type ink cell system that may be used to measure the conductivity of a static pool of ink.

One or more aspects of the present disclosure are described with reference to the drawings, wherein like reference numerals are generally utilized to refer to like elements throughout, and wherein the various structures are not necessarily drawn to scale. In the following description, for purposes of explanation, numerous specific details are set forth in order to provide a thorough understanding of one or more aspects of the disclosure herein. It may be evident, however, that one or more aspects of the disclosure herein may be practiced with a lesser degree of these specific details. In other instances, well-known structures and devices are shown in block diagram form to facilitate describing one or more aspects of the disclosure herein.

Generally speaking, liquid electro-photography ink is a dispersion of electrically chargeable particles in a dielectric liquid media. Upon applying an electrical field, the particles become electrically charged and drift along the electrical field. Observation shows that the electrical conductivity of such an ink is strongly dependent on the strength of the applied electrical field—being low at low intensity field (typically below 50V/mm) and substantially higher at high intensity field (typically above 500V/mm). Accordingly, distinction is made between conductivities measured at low electrical field and high electrical field.

Observation also shows that when the ink particles are deprived from being replenished, as the particles drift to one of the electrodes, the measured current falls off reaching a constant value where substantially no particles are left (depleted) in the liquid between the electrodes.

For purposes of the disclosure, the following terms shall have the following meanings:

The term "a" or "an" entity refers to one or more of that entity. As such, the terms "a" or "an", "one or more of" and "at least one" can be used interchangeably herein.

"High field conductivity" is defined as the conductivity measured at the moment of applying the high intensity electrical field before particle depletion can take place.

"Low field conductivity" is defined as conductivity measured at low intensity field.

"DC conductivity" is defined as the conductivity measured after the current has leveled off because the measured current has achieved a substantially constant value.

"Particle conductivity" is defined as the difference between the high field conductivity of the ink and the low field conductivity as this difference is attributed to the particles and is referred to as "particle conductivity" as observation shows that after removing the particles from the ink (e.g., by separation in centrifuge) the remaining particle-less fluid essentially exhibits the same high field conductivity as the low field conductivity measured in the ink before removal of the particles. Particle conductivity is calculated as the product of the particle concentration (e.g., the number of particles per unit volume) multiplied by the charge carried by a single particle and by the mobility of the particles.

"Mobility" is defined as the ratio of the drift velocity of the particle to the applied electrical field strength.

The time integral of the current induced by high electrical field and corrected for the currents due to low field conductivity and DC conductivity represents the electrical charge carried by the particles.

Thus, the measurement of the different types of conductivity provides not only direct electrical properties but also valuable ink characteristics, such as charge concentration and particle concentration.

Referring to FIG. 1, for example, a laboratory type ink cell system 10 is illustrated that may be used to measure the conductivity of a static pool of ink. The ink comprises a dispersion 20 of ink particles 22 within a dielectric liquid media. The ink dispersion 20 that is to be measured is placed within an ink cell 24 between a pair of conductive electrodes 25 comprising a positive (+) electrode 26 and a negative (−) electrode 28 connected to a respective positive (+) terminal 32 and a negative (−) terminal 34 of a high voltage supply and low level current meter 30 of the ink cell system 10.

In operation, a relatively high voltage from the voltage supply 30 is applied to the electrode pair 25 of the ink cell 24. The ink particles 22 within the ink dispersion 20 are charged and briefly permit a current to conduct as the particles drift along the electric field between the electrodes 26 and 28, as discussed above in regard to the "high field conductivity". The current which conducts between the electrode pair 25 is measured by the low level current meter 30 and may be used to determine several characteristics associated with the conductivity of the ink dispersion 20 within the ink cell 24.

As was also discussed above in regard to the "low field conductivity", observation shows that when the ink particles 22 are deprived from being replenished (such as in the static ink cell 24), as the particles 22 drift to one of the electrodes, the measured current falls off reaching a constant value (e.g., "DC conductivity") when few to no particles remain dispersed (depleted) within the liquid ink dispersion 20 between the electrodes 26/28.

Figure 2:
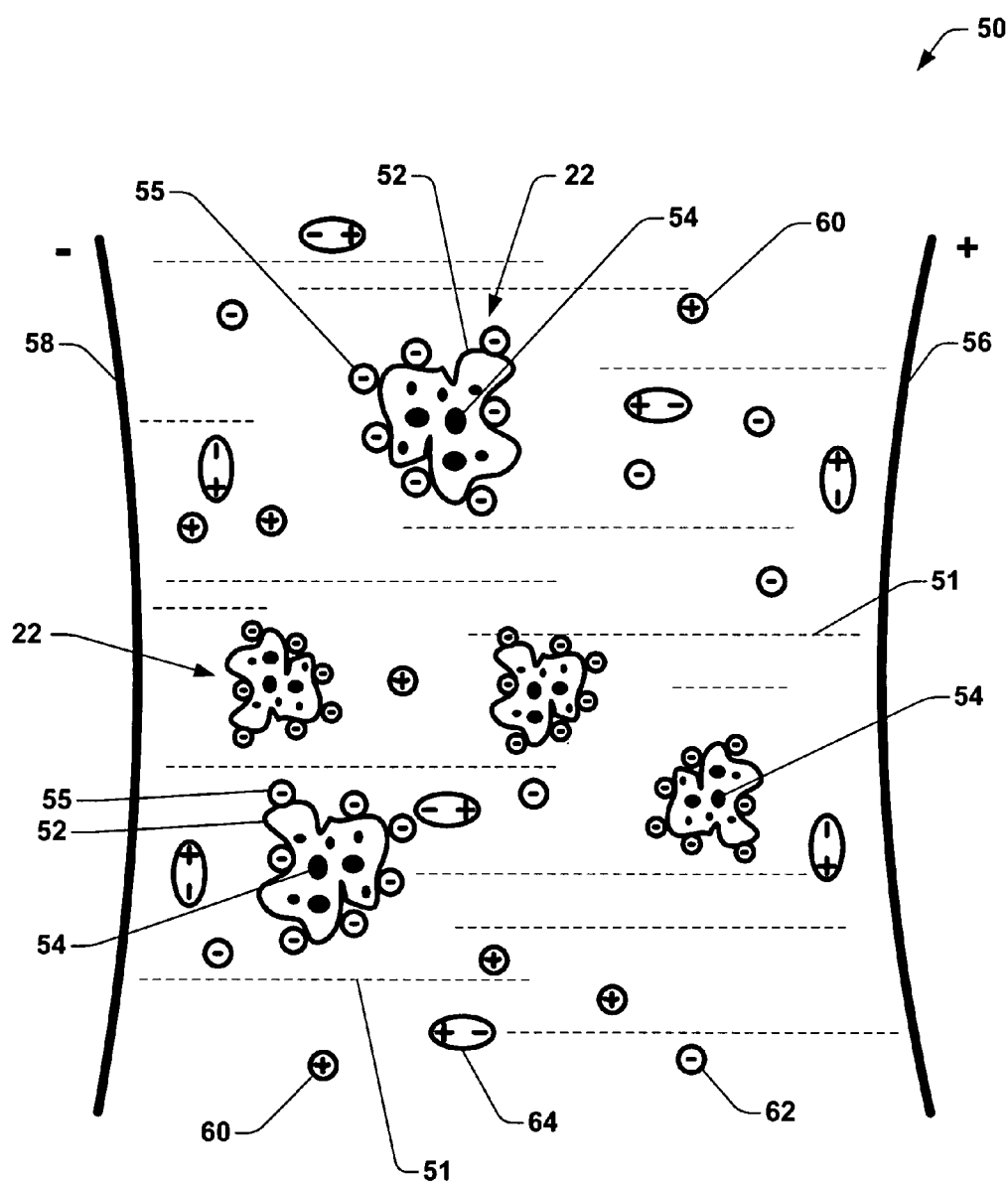
FIG. 2 is a simplified functional schematic diagram of the basic operation of an Electro-Ink such as may be used in liquid electro-photography, comprising a dispersion of electrically chargeable particles in a dielectric liquid media.

FIG. 2 further illustrates the basic operation of an Electro-Ink 50 such as may be used in liquid electro-photography. Liquid electro-photography ink 50 comprises a dispersion of electrically chargeable ink particles 22 in a dielectric liquid media or carrier liquid (e.g., imaging oil) 51. The ink particles 22 of the Electro-Ink 50 further comprise a toner particle 52 having a pigment 54, wherein the ink particles 22 may receive a negative charge 55 as a result of an electric field induced between a positive (+) electrode 56 and a negative (−) electrode 58. If the fluid can be ionized, it may also contain positive ions 60 and/or negative ions 62 as a result of the induced electric field between the electrode pair. The Electro-Ink 50 may further contain a specific type of surface active agent known as charge directors 64, which may be added to the ink to promote the ability of the ink particles 22 to acquire electrical charge.

As previously discussed, when the ink and the ink particles 22 are stationary or are otherwise deprived from being replenished (such as in the static ink cell 24 of FIG. 1), the charged particles 22 (e.g., receiving negative charge 55) drift to one of the electrodes (e.g., negatively charged particles 22 are attracted to the positive electrode 56). When substantially all of the particles have drifted to the electrodes, the measured current falls off reaching a constant value (e.g., "DC conductivity").

In one embodiment for the electro(-photo-)graphic process, one of the electrodes such as electrode 56 may be used as an "electro-photographic" plate or photo imaging plate (PIP) 56, carrying a latent image in the form of a corresponding spatial distribution of electrical charges or potentials. In this embodiment, the other electrode 58 may then be used as the developer 58 that provides the ink 22 and pigment 54 in the toner particles 52, which is then attracted to the spatial distribution of electrical charges representing the latent image.

Figure 3:
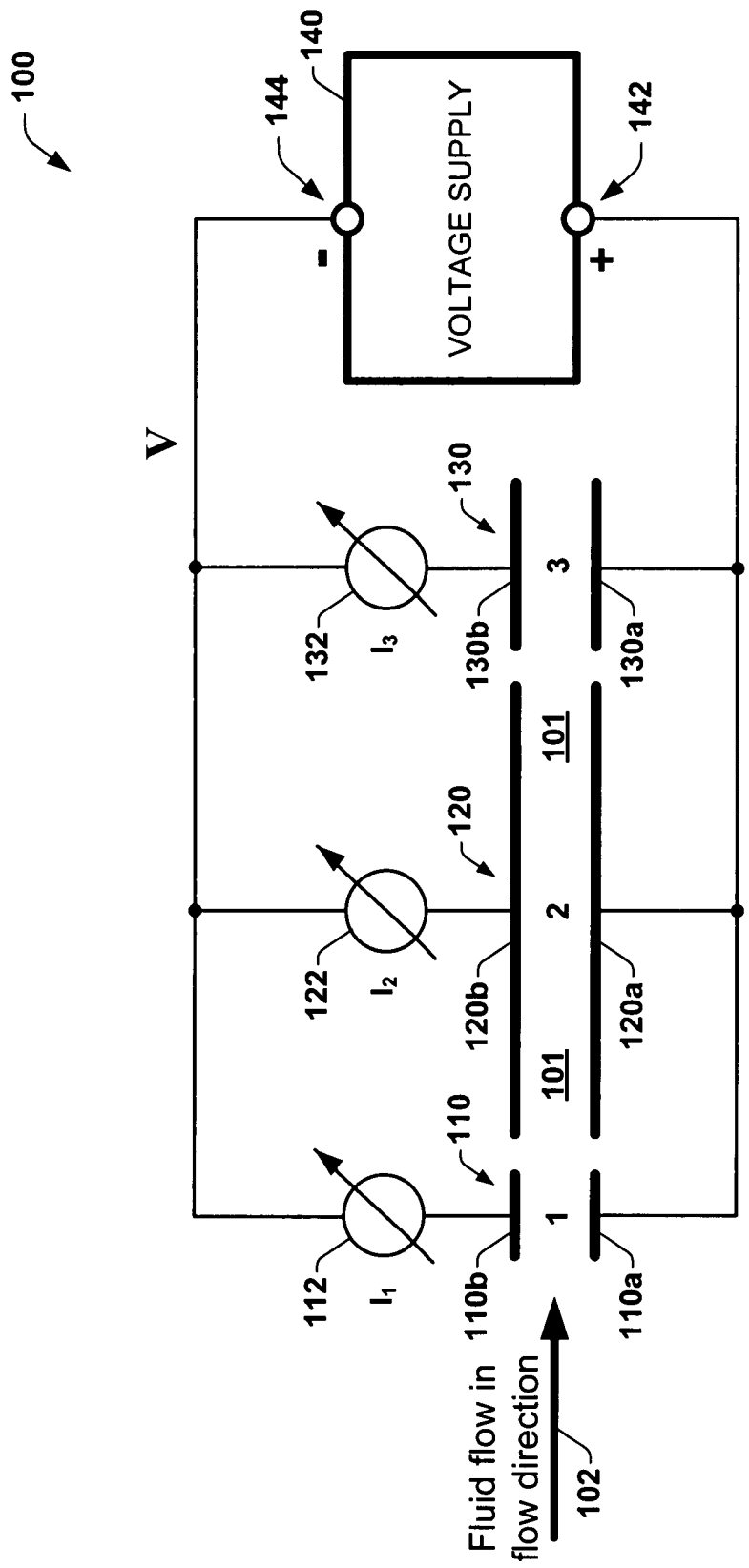
FIG. 3 is a simplified schematic diagram of one exemplary embodiment of a conductivity and charge meter system configured to monitor and determine one or more characteristics of a flowing fluid, such as the conductivity of a flowing ink in accordance with one or more aspects and/or embodiments of the disclosure herein.

FIG. 3 illustrates one exemplary embodiment of a conductivity and charge meter system 100 configured to monitor and facilitate the determination of one or more characteristics of a flowing fluid, such as the conductivity of a flowing ink 102 in accordance with one or more aspects and/or embodiments of the disclosure herein.

One embodiment of the conductivity and charge meter system 100 comprises three (or more) electrode pairs that are placed in a fluid (e.g., ink) containing charged particles. The fluid 101 is forced or otherwise caused to flow in a direction 102 between respective first and second plates (e.g., 110a/110b, 120a/120b, and 130a/130b) of the electrode pairs (e.g. 110, 120, and 130). The electrode pairs (e.g. 110, 120, and 130) are biased by a DC voltage V (e.g., applied by a positive (+) terminal 142 and a negative (−) terminal 144 of a voltage supply 140) such that by the time the fluid flows by the third (last) electrode pair 130 substantially all of the charged particles are removed from the fluid 101 (e.g., by being attracted to the second pair of plates 120a/120b of the second (middle/intermediate) electrode pair 120). While the fluid flows between the respective first and second plates (e.g., 110a/110b, 120a/120b, and 130a/130b) of the electrode pairs (e.g. 110, 120, and 130), a corresponding DC current is monitored and measured between the plates of each of the electrode pairs, yielding a first current $I_1$ measured at current meter 1 (112), a second current $I_2$ measured at current meter 2 (122), and a third current $I_3$ measured at current meter 3 (132) based upon the applied DC voltage V from the voltage supply 140. The DC current measurements $I_1$, $I_2$, and $I_3$ are then used to determine one or more conductivity characteristics or another such characteristic of the fluid based on a variety of factors and/or conditions associated with the measurement. Such factors and/or conditions may include, among others, the distance (d) between the plates, the cross-sectional area of the plates (A), and the applied voltage V, for example, as will be discussed further infra.

In this manner, and as the fluid 101 enters the conductivity and charge meter embodiment 100 of FIG. 3 in flow direction 102, an initial fluid conductivity measurement taken between the first and second plates 110a/110b of the first electrode pair 110 reflects a high concentration of charged particles in the fluid (e.g., for the "high field conductivity" measurement), while a fluid conductivity measurement taken between the first and second plates 130a/130b of the third (last) electrode pair 130 reflects a substantially low concentration of charged particles in the fluid (e.g., for the "DC conductivity" measurement). These conductivity measurements, as well as a "low field conductivity" measurement between the first and second plates 120a/120b of the second electrode pair 120 can then be used to determine additional characteristics of the fluid, which can affect the quality of the printing process.

Thus, in this example, a fluid such as ink is pumped or otherwise directed to flow between three (or more) electrode pairs, wherein the first electrode pair 110 has a short length in the direction 102 of the fluid flow, the second electrode pair 120 has a long length along the flow direction 102, and the third electrode pair 130 has an arbitrary length along the flow direction 102. For example, it will be appreciated that a peristaltic pump or another such pumping means may be used to pump the fluid between the plates of the three electrode pairs. By applying both a high and low value DC voltage (e.g., alternately) across the electrode pairs, two corresponding DC current values may be measured between the plates of the respective electrode pairs.

Further, the length of the first short electrode pair 110 is such that no significant particle depletion takes place during the time that the particles pass this electrode pair 110, yet during such time, adequate charge collection occurs to enable current measurements therefrom. The length of electrode pair 120 is long enough to assure substantially total removal of the particles (referred to as polarization) from the fluid (e.g., ink) during passage of the fluid therebetween. Finally, the third electrode pair 130 need only be long enough to provide an adequate minimum charge collection for current measurement therefrom.

Based on the DC current measurements from each of the electrode pairs, one or more conductivity or other such characteristics of the fluid may be determined, including specific charge, mobility, and concentration of the charged particles, for example. The charged particles may or may not be native to the fluid, but such particles are generally an integral part of the fluid when manufactured for use in the electro(-photo-) graphic process, wherein the particles may also carry colorants and/or binders.

Figure 4:
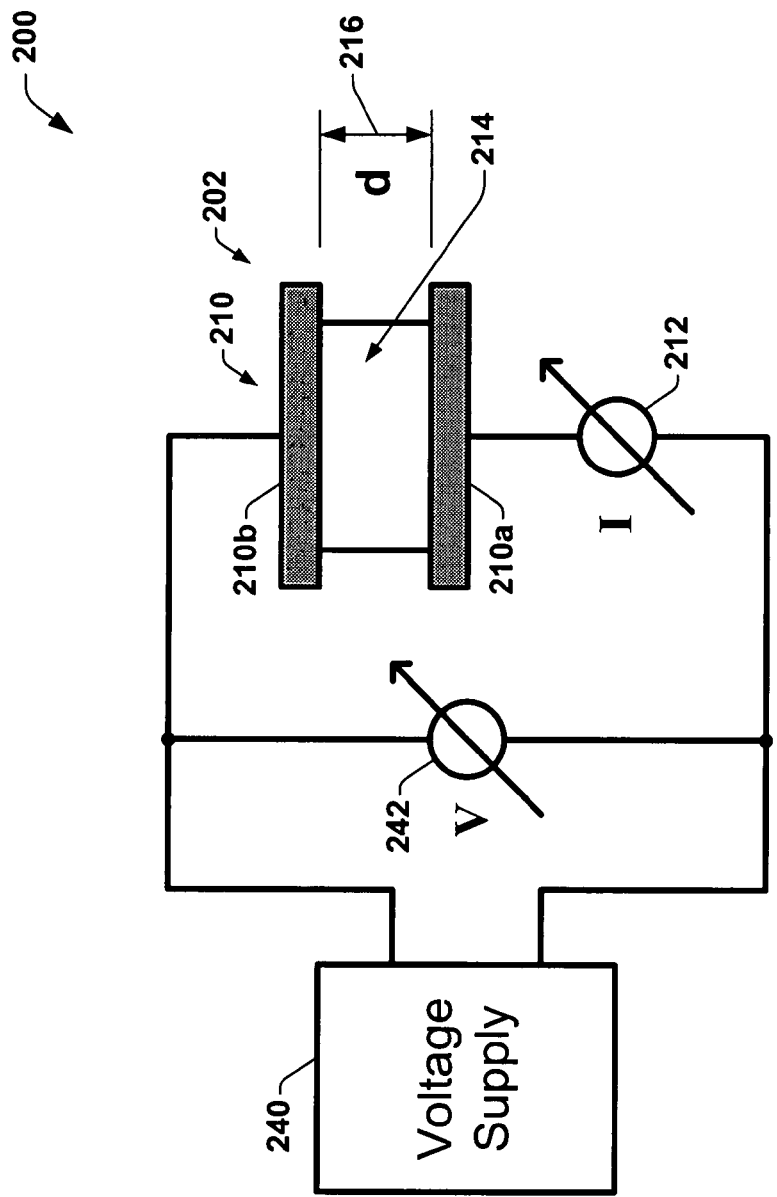
FIG. 4 is a simplified functional schematic diagram of a measuring system that may be used to measure a fluid characteristic, such as the conductivity of a static fluid specimen and an equation that may be used for such measurement.

FIG. 4 illustrates a measuring system 200 that may be used to measure one or more characteristics such as the conductivity of a static fluid specimen and an equation that may be used for such measurement. Similar to the ink cell 10 of FIG. 1, the measuring system 200 of FIG. 4 comprises a measuring cell 202 having a pair of electrodes 210 comprising a first electrode or plate 210a and a second electrode or plate 210b which are spaced apart by a distance d 216 on either side of the specimen 214 having a cross-sectional area A as seen by the plates 210a/210b.

Voltage supply 240 is electrically connected to the plates 210a/210b of the measuring cell 202, and supplies a voltage V 242 to the electrode pair 210. As a result of the applied voltage 242, a current I 212 can be measured between the first plate 210a and the second plate 210b. Based upon the measured current I 212, a conductivity a may be determined according to the equation:

$$\sigma = \frac{I/A}{V/d} = \frac{I}{V} \cdot \frac{d}{A}$$

where

σ=conductivity of the sample (in units of pmhO/cm)
I=current measured between the plates and thru the sample
A=cross-sectional area of the measured sample exposed to the plates
d=distance between the plates
V=voltage applied to the plates of the sample cell.

Figure 5A:
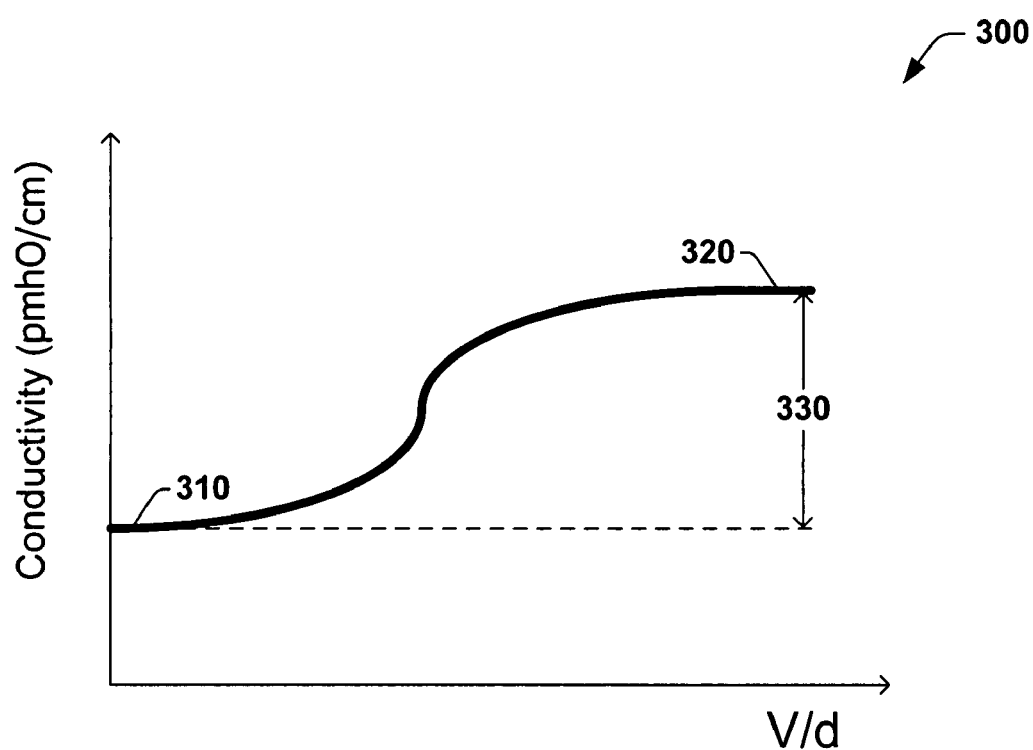
FIGS. 5A and 5B are plots of several fluid characteristics which may, for example, be measured and determined using the system embodiments of FIGS. 1, 3, and 4 in accordance with one or more aspects of the disclosure herein.
Figure 5B:
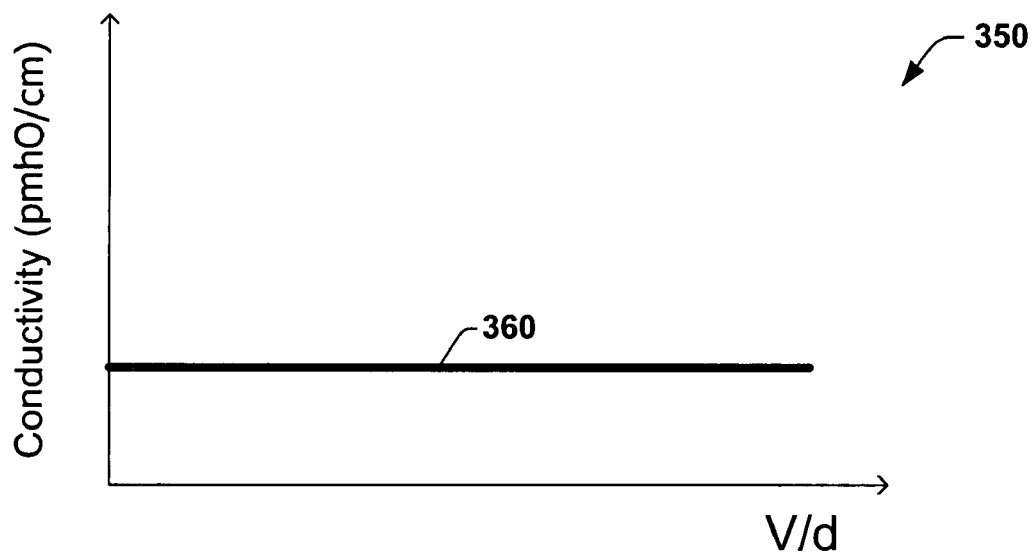

FIGS. 5A and 5B illustrate exemplary plots 300 and 350, respectively, of several fluid characteristics which may, for example, be measured and determined using the system embodiments of FIGS. 1, 3, and 4 in accordance with one or more aspects of the disclosure herein.

For example, FIG. 5A illustrates an exemplary plot 300 of the conductivity (in pmhO/cm) of a 2% fluid (the particles comprise 2% of the fluid) as a function of an applied voltage V per unit distance d, the voltage V applied to a sample cell such as sample cell 202 of FIG. 4. When the applied voltage V is applied at a lower voltage level, a "low field conductivity" 310 results, and when a higher voltage level is applied to the sample, a "high field conductivity" 320 is provided. The difference between the "high field conductivity" 320 and the "low field conductivity" 310 is known as the "particle conductivity" 330.

FIG. 5B, illustrates another exemplary plot 350 of the conductivity (in pmhO/cm) of a fluid or carrier fluid without particles in the fluid sample (e.g., depleted of particles), the conductivity 360 measured as a function of an applied voltage V per unit distance d, the voltage V applied to a sample cell such as sample cell 202 of FIG. 4.

Figure 6A:
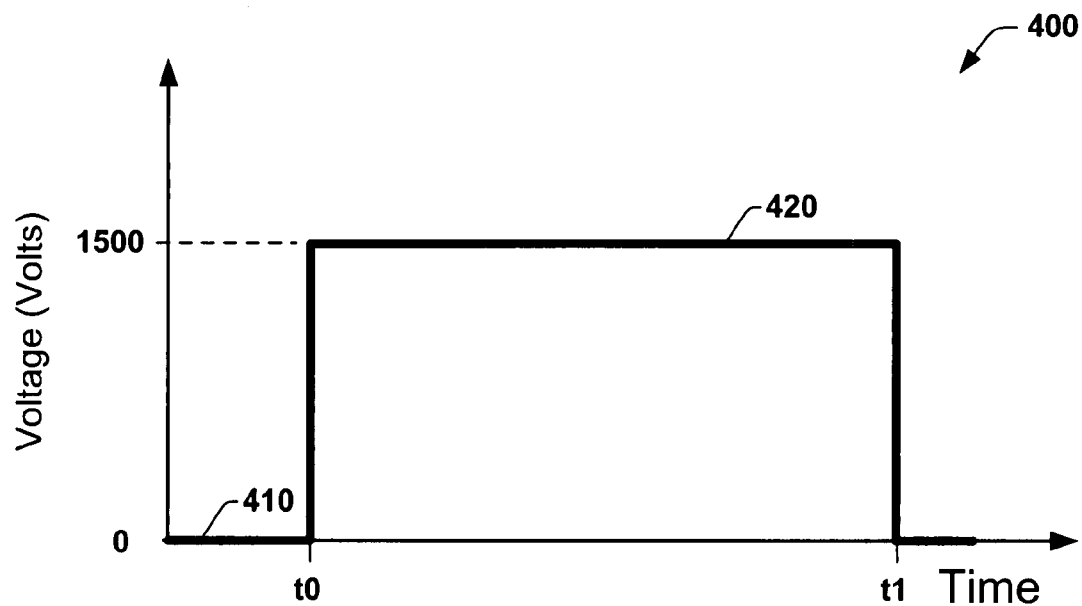
FIGS. 6A and 6B are plots of an applied high field voltage and a corresponding conductivity response that may be obtained during a measurement of one or more fluid characteristics which may, for example, be determined using the system embodiments of FIGS. 1, 3, and 4 in accordance with one or more aspects of the disclosure herein.
Figure 6B:
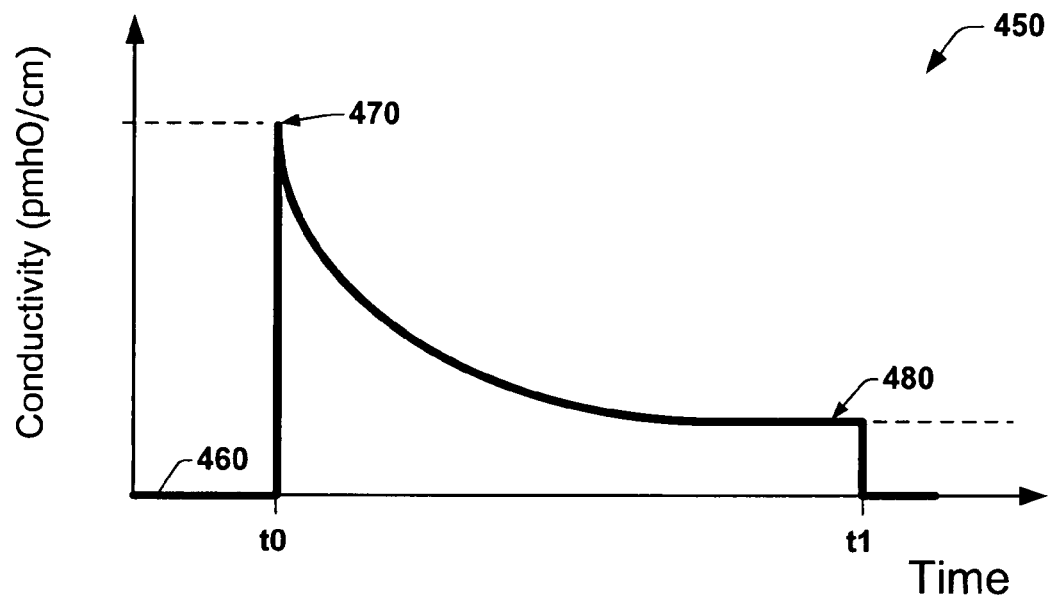

FIGS. 6A and 6B illustrate exemplary plots 400 and 450, respectively, of an applied high field voltage and a corresponding conductivity response that may be obtained during a measurement and determination of one or more fluid characteristics, for example, using the system embodiments of FIGS. 1, 3, and 4 in accordance with one or more aspects of the disclosure herein.

For example, FIG. 6A illustrates a high field voltage waveform 400, wherein a high voltage is applied to a measurement cell such as sample cell 202 of FIG. 4. Prior to time t0, the voltage waveform 400 is at about 0 volts as shown at 410. In response to this applied low voltage, and as shown in the plot 450 of FIG. 6B, the conductivity (corresponding to the measured current) is also at about 0 pmhO/cm at 460.

Between times t0 and t1, the voltage 400 is stepped up to a "high field voltage" level of about 1500 volts, for example, at 420 across the plates of the cell having spacing distance d (e.g., 216 of FIG. 4) of about 1 mm, for example. Thus, in the embodiment, the electric field strength equals:

Electric field strength=1500V/1 mm=1.5V/μ

In response to this step function of the high field voltage 420 applied at t0, the conductivity spikes to a "high field conductivity" level as shown at 470 in FIG. 6B. As the high field voltage level is maintained at the 420 level, the charged particles (e.g., 22 of FIG. 2) within the fluid (e.g., 51 of FIG. 2) are substantially all attracted toward the oppositely charged electrode (e.g., positive electrode 56 of FIG. 2) between times t0 and t1. By time t1 (e.g., after about 8 seconds), substantially all of the charged particles 22 have been depleted from the fluid and the conductivity of the fluid attains a substantially steady-state or "DC conductivity" level 480. In this manner, numerous other fluid and particle characteristics may be measured and/or determined.

Figure 7:
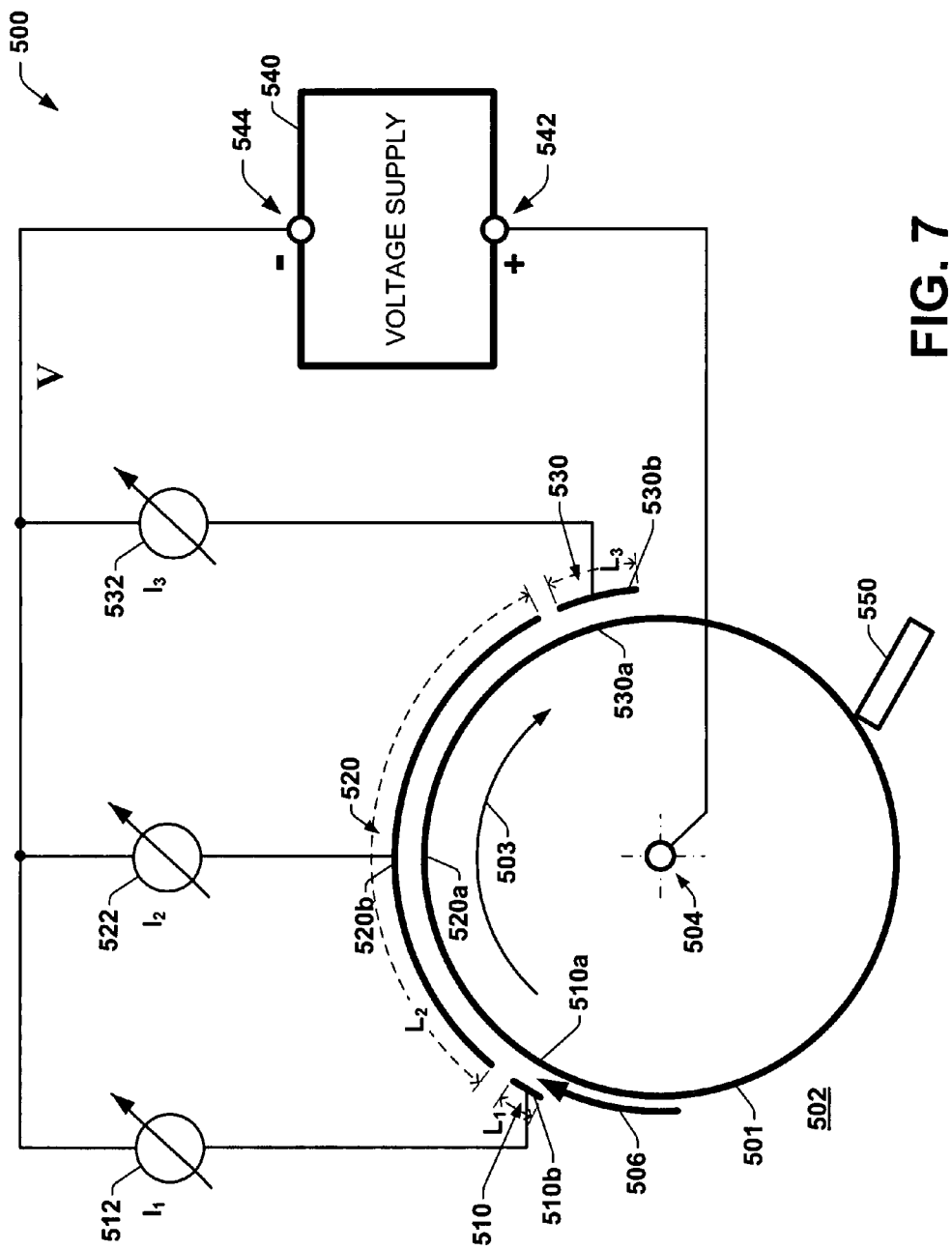
FIG. 7 is a simplified schematic diagram of an exemplary embodiment of a conductivity and charge meter system configured to monitor and determine one or more characteristics of a flowing fluid, such as the conductivity of a flowing ink caused to flow between several electrode pairs using a rotating drum in accordance with one or more aspects and/or embodiments of the disclosure herein.

Accordingly, FIG. 7 illustrates an exemplary embodiment of a conductivity and charge meter system 500 configured to monitor and determine one or more characteristics of a flowing fluid, such as ink, that is caused to flow between several electrode pairs by using a rotating drum 501.

In FIG. 7, a drum 501 rotates within a fluid 502 (e.g., Electo-Ink 50 of FIG. 2) containing charged particles (e.g., 22 of FIG. 2). As the drum 501 rotates in a direction 503 about a center point 504 which is connected to a positive terminal 542 of a voltage supply 540, the fluid 502 is carried along the surface of the drum in a circular flow direction 506 between first and second plates 510a/510b, 520a/520b, and 530a/530b of three respective electrode pairs 510, 520, and 530. In this example 500, the first plates 510a, 520a, and 530a of the respective electrode pairs 510, 520, and 530 are combined together into a single or common plate comprised of the surface of the drum 501.

In particular, the fluid 502 is made to initially flow between a relatively short (e.g., having a length $L_1$) first pair of electrodes 510 comprising first and second plates 510a and 510b monitored by current meter 1 (512). Thereafter, the fluid 502 flows between a relatively long (e.g., having a length $L_2$) second pair of electrodes 520 comprising first and second plates 520a and 520b monitored by current meter 2 (522). Finally, the fluid 502 flows between a relatively arbitrary length (e.g., having a length $L_3$) third pair of electrodes 530 comprising first and second plates 530a and 530b monitored by current meter 3 (532). Accordingly, the three current meters 512, 522, and 532 are connected to the negative terminal 544 of the voltage supply 540 in order to provide current measurements $I_1$, $I_2$, and $I_3$ which flow between the first and second plates of the respective electrode pairs 510, 520, and 530 based upon an applied voltage V provided by voltage supply 540. It will be appreciated that while three (3) electrode pairs are illustrated in FIG. 7 (and FIG. 3), that any suitable number of electrode pairs may be used.

In operation, the fluid 502 flowing between the first and second plates 510a/510b of the first electrode pair 1 (510) provides the first current measurement $I_1$ while the fluid 502 contains a maximum or full concentration of charged particles (e.g., 22 of FIG. 2). Accordingly, the length $L_1$ of the first electrode pair 510 is such that few to no charged particles polarize onto the drum 501 configured as the positive plate (e.g., first plate 510a, 520a, and 530a) of the first, second, and third electrode pairs 510, 520, and 530, respectively. The length $L_1$ of the first electrode pair 510 is, however, sufficient to allow adequate charge collection to enable the $I_1$ current measurement. Accordingly, if a high field voltage V (e.g., 420 of FIG. 6A) is applied by voltage supply 540 to the first electrode pair 1 (510), a "high field conductivity" (e.g., 470 of FIG. 6B) may be determined based on the first current measurement $I_1$ of the first electrode pair 1 (510).

As the fluid 502 flows between the first and second plates 520a/520b of the substantially longer second electrode pair 2 (520), the fluid 502 loses substantially all of the charged particles (e.g., 22 of FIG. 2), during which time the second current measurement $I_2$ of the fluid is provided. Accordingly, the length $L_2$ of the second electrode pair 520 is sufficient to allow substantially all of the charged particles to be polarized or plated out of the fluid 502 onto the drum 501 configured as the positive plate 520a of the second electrode pair 520. Accordingly, if a high field voltage V is applied by voltage supply 540, to the second electrode pair 2 (520), a current flow and corresponding conductivity resembling the waveform 450 of FIG. 6B could (potentially) be viewed in a given sample of the fluid 502 moving along the length of the second electrode pair (520).

Thus, by the time the fluid 502 flows between the first and second plates 530a/530b of the third electrode pair 530, substantially all of the charged particles (e.g., 22 of FIG. 2) have been removed from the fluid, and the third current measurement $I_3$ of the fluid is provided. Accordingly, if a high field voltage V is applied by voltage supply 540 to the third electrode pair 530, a "DC conductivity" (e.g., 480 of FIG. 6) may be determined based on the third current measurement $I_3$ of the third electrode pair 3 (530). Because substantially all of the charged particles (e.g., 22 of FIG. 2) have been removed from the fluid 502 and plated onto the drum 501 as the fluid flowed between the polarized plates of the respective first, second, and third electrode pairs 510, 520, and 530, a wiper 550 is utilized in the illustrated example to remove the charged particles from the drum 501 and to reintroduce them back into the fluid 502. Thus, the wiper 550 and the rotation of the drum 501 serve to mix the charged particles back into the fluid 502, such that the particle concentration of the fluid 502 at the first electrode pair 510 is substantially back to the original full concentration level.

Again, as in FIG. 3, by applying both a high and a low value DC voltage (e.g., Vhi and Vlo), for example, alternately across the electrode pairs of FIG. 7, two corresponding DC current values (e.g., $I_{1hi}$ and $I_{1lo}$, $I_{2hi}$ and $I_{2lo}$, and $I_{3hi}$ and $I_{3lo}$) may be measured between the first and second plates 510a/510b, 520a/520b, and 530a/530b of the respective electrode pairs 510, 520, and 530.

It will be appreciated that other such configurations and pumping means, such as a peristaltic pump, may be utilized to move the fluid between the plates of the electrode pairs 510, 520, and 530. In addition, the wiper 550 may be replaced by another particle removal means such as a turbulence inducing surface and/or a jet of fluid that blasts the charged particles from the drum 501, for example. Further, the surface of the drum 501 or the second plates 510b, 520b, and 530b may have various grooves or surface features that enhance or otherwise accommodate the movement of the fluid flow 506, enhance current measurements, and/or improve characteristic determinations, for example.

Although the distance between the first and second plates of the three electrode pairs are illustrated as being the same, it will also be appreciated that the distances between the first and second plates of the three electrode pairs could be different.

Also, additional electrode pairs and current meters may be added to those illustrated.

In one implementation of the example of FIG. 7, the following parameters may be utilized:

The length $L_1$ of the first electrode pair 1 (e.g., 510) is about 5 mm;

The length $L_2$ of the second electrode pair 2 (e.g., 520) is about 50 mm;

The length $L_3$ of the third electrode pair 3 (e.g., 530) is about 55 mm;

A width of all the electrodes (e.g., 510, 520, and 530), measured perpendicular to the flow direction (e.g., 506) is about 50 mm.

The drum (e.g., 501) or cylindrical common electrode has a diameter of about 100 mm and width of about 60 mm.

A gap between the second plates (e.g., 510b, 520b, and 530b) of the electrode pairs and the cylinder (e.g., drum 501) is about 1 mm.

A gap between the first electrode pair 1 (e.g., 510) and the second electrode pair 2 (e.g., 520), or between the second electrode pair 2 (e.g., 520) and third electrode pair 3 (e.g., 530) is about 1 mm.

A rotation rate of the cylinder (e.g., drum 501) is about 20 revolutions per minute.

A low voltage $V_{Lo}$ applied on the first electrode pair 1 (e.g., 510) is about 30 V.

A duration of the low voltage $V_{Lo}$ pulse is about 2 sec.

A pause with zero voltage after the application of the low voltage $V_{Lo}$ pulse is about 1 sec.

A high voltage $V_{Hi}$ applied on any of the first, second, or third electrode pairs (e.g., 510, 520, and 530) is about 1,500V.

A duration of the high voltage $V_{Hi}$ pulse is about 2 sec.

A pause with zero voltage after the application of the high voltage $V_{Hi}$ pulse is about 1 sec.

Grounded guard electrodes (e.g., that are connected to ground potential through the current measuring devices) may be provided around the second plates of the electrode pairs, so that uncontrolled electrical current flow will have little to no effect on current measurements.

Accordingly, regardless of the measurement mechanism used, such as embodiment 100 of FIG. 3 or embodiment 500 of FIG. 7, the current measurement data is analyzed, for example, by a computer or another such analyzer to determine one or more characteristics or parameters of the fluid.

FIGS. 8-11 illustrate an exemplary methodology 600 that facilitates monitoring and determining a conductivity of a flowing fluid based on current measurement data in accordance with one or more aspects of the disclosure herein, such as may be used in the conductivity and charge meter system 500 of FIG. 7, for example.

Although the methodology 600 is illustrated and described hereinafter as a series of acts or events, it will be appreciated that the illustrated ordering of such acts or events is not to be interpreted in a limiting sense. For example, some acts may occur in different orders and/or concurrently with other acts or events apart from those illustrated and/or described herein. In addition, not all illustrated acts may be required to implement one or more aspects and/or embodiments of the description herein. Further, one or more of the acts may be carried out in one or more separate acts and/or phases.

Figure 8:
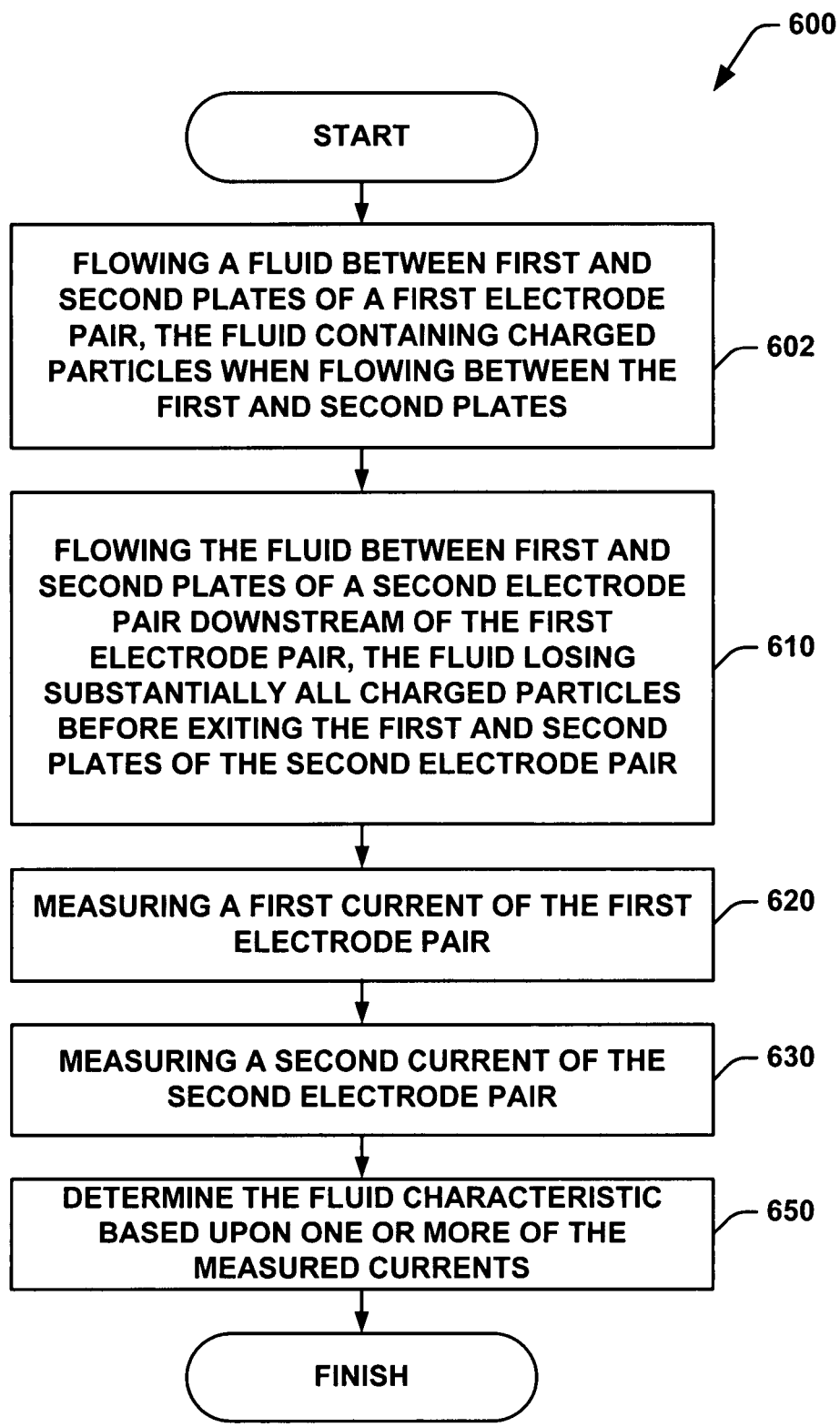
FIGS. 8-11 are flow diagrams illustrating one or more embodiments of an exemplary methodology operative to monitor and determine a conductivity of a flowing fluid based on current measurement data in accordance with one or more aspects of the disclosure herein.

With reference to FIG. 8, the method 600 begins at 602 where a fluid (e.g., 502 of FIG. 7) containing charged particles (e.g., 22 of FIGS. 1 and 2) is made to flow between first and second plates (e.g., 510a/510b) of a first electrode pair (e.g., 510). Then, at 610, the fluid (e.g., 502) flows between first and second plates (e.g., 520a/520b) of a second electrode pair (e.g., 520) located downstream of the first electrode pair (e.g., 510), the fluid losing substantially all charged particles when flowing between the first and second plates (e.g., 520a/520b) of the second electrode pair (e.g., 520).

At 620, a first current (e.g., $I_1$) of the first electrode pair (e.g., 510) is measured. A second current (e.g., $I_2$) of the second electrode pair (e.g., 520) is measured at 630.

At 650, the fluid characteristic (e.g., a conductivity of fluid 502) is determined based upon one or more of the currents (e.g., $I_1$, and/or $I_2$) measured between the first and second plates (e.g., 510a/510b, and 520a/520b) of the respective first and second electrode pairs (e.g., 510 and 520).

Thus, a high field conductivity $\sigma_{Hi}$ (e.g., 470 of FIG. 6B) may be determined from a measured first current (e.g., $I_1$) measured between the first and second plates (e.g., 510a/510b) of the first electrode pair (e.g., 510), for example, according to:

$$\sigma_{Hi} = I_1/V_{Hi} * d/(L_1 * D)$$

where $I_1$ denotes the current measured between the first and second plates of the first electrode pair, $V_{Hi}$ denotes a high voltage applied to the first electrode pair, $L_1$ denotes a length of the first electrode pair in the direction of the fluid flow, D denotes the width of the first electrode pair, and d denotes the gap between the first and second plates of the first electrode pair.

Figure 9:
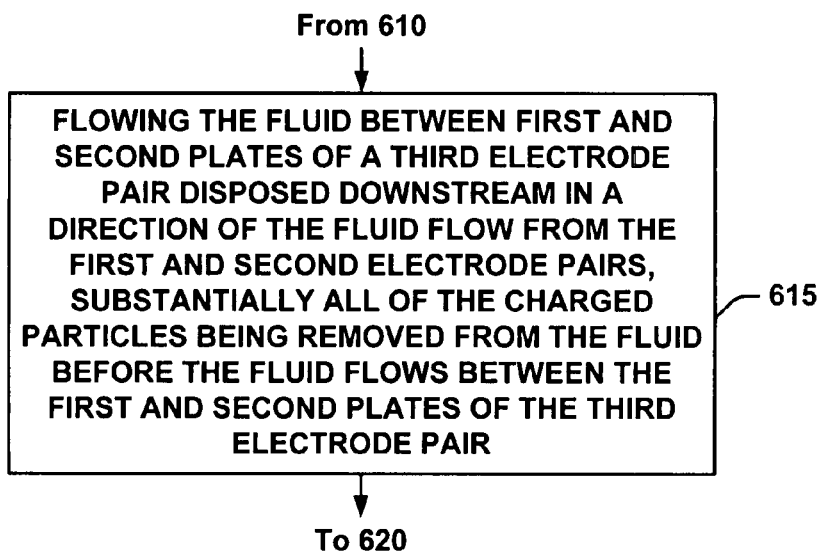

Alternately, with reference to FIG. 9, after the fluid flows between the plates of the second electrode pair at 610 of the method 600, 615 comprises flowing the fluid (e.g., 502) between first and second plates (e.g., 530a/530b) of a third electrode pair (e.g., 530) with the second electrode pair located between the first and third electrode pair (e.g., 510 and 530), wherein substantially all of the charged particles (e.g., 22 of FIGS. 1 and 2) have been removed from the fluid (e.g., at 480 of FIG. 6B) when the fluid flows between the first and second plates (e.g., 530a/530b) of the third electrode pair (e.g., 530).

Figure 10:
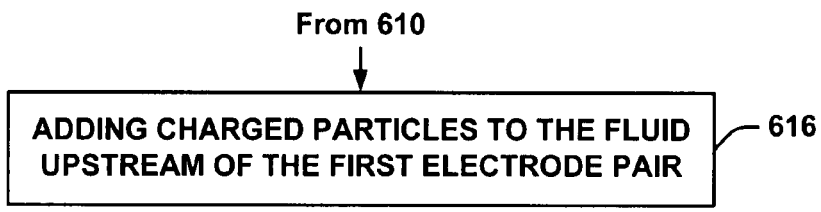

Further, with reference to FIG. 10, after substantially all of the charged particles have been removed from the fluid while flowing between the plates of the second electrode pair at 610 of the method 600, 616 comprises adding or reintroducing substantially all of the charged particles (e.g., 22 of FIGS. 1 and 2) back into the fluid (e.g., at 480 of FIG. 6B) upstream of the first electrode pair (e.g., 510). For example, this may be accomplished with the aid of the wiper 550 illustrated in FIG. 7.

Figure 11:
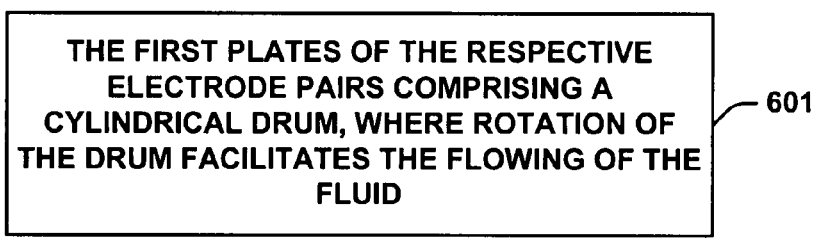

Finally, with reference to FIG. 11, 601 of the method 600 comprises utilizing a rotating cylindrical drum (e.g., 501) to facilitate the flowing of the fluid (e.g., 502) and to implement the first plates (e.g., 510a, 520a, 530a) of the respective electrode pairs (e.g., 510, and/or 520, and/or 530). For example, as discussed above with respect to drum 501 of FIG. 7, the rotation of the drum 501 can provide a pumping action to force the fluid 502 between the electrode pairs to enable the current measurements, and can also be used to mix the particles back into the fluid 502 after removal from the drum 501 by the wiper 550.

One or more other such characteristics may also be determined.

For example, a low field conductivity may be determined from the current measured from the first electrode pair according to:

$$\sigma_{Lo} = I_1/V_{Lo} * d/(L_1 * D)$$

where $I_1$ denotes the current measured between the first and second plates of the first electrode pair;

$V_{Lo}$ denotes a low voltage applied to first electrode pair;

$L_1$ denotes a length of first electrode pair in the direction of the fluid flow;

D denotes a width of first electrode pair; and d denotes a gap between the first and second plates of the first electrode pair.

In another example, a DC conductivity may be determined from a current measured from the third electrode pair according to:

$$\sigma_{dc} = I_3/V_{Hi} * d/(L_3 * D)$$

where $I_3$ denotes the current measured between the first and second plates of the third electrode pair;

$V_{Hi}$ denotes a high voltage applied to third electrode pair;

$L_3$ denotes a length of third electrode pair in the direction of the flow;

D denotes a width of third electrode pair; and d denotes a gap between the first and second plates of the third electrode pair.

In yet another example, a total charge of the fluid per unit volume may be determined from a current measured from respective first, second and third electrode pairs according to:

$$Q_V = (I_1 + I_2 - [L_1 + L_2]/L_3 * I_3)/(v * D * d)$$

where $I_1$ denotes the current between the first and second plates of the first electrode pair;

$I_2$ denotes the current between the first and second plates of the second electrode pair;

$I_3$ denotes the current between the first and second plates of the third electrode pair;

$L_1$ denotes a length of the first electrode pair in the direction of the flow;

$L_2$ denotes a length of the second electrode pair in the direction of the flow;

$L_3$ denotes a length of third electrode pair in the direction of the flow;

D denotes a width of the respective first, second and third electrode pairs;

d denotes a gap between the first and second plates of the first, second and third electrode pairs; and v denotes a linear speed of the fluid flow.

In still another example, a particle conductivity may be determined from the current measured from the first electrode pair according to:

$$\sigma_{Part} = \sigma_{Hi} - \sigma_{Lo}$$

where $\sigma_{Hi}$ denotes the high field conductivity,
$\sigma_{Lo}$ denotes the low field conductivity.

In another example, a mobility of the charged particles may be determined according to:

$$\mu = \sigma_{Part}/Q_V$$

where
$\sigma_{Part}$ denotes the particle conductivity;
$Q_V$ denotes total charge of the fluid (e.g., 502) per unit volume.

In yet another example, a volume concentration of the charged particles may be determined according to:

$$C_V = k*Q^2_V/\sigma_{Part}$$

where
$Q_V$ denotes total charge of the fluid per unit volume, being determined from a current measured from the respective first, second and third electrode pairs;
$\sigma_{Part}$ denotes the particle conductivity;
k is a proportionality factor that in the theoretical limits of uniform spherical particles can be calculated as:

$$k = 1/(6*\pi*\eta*r)$$

where
$\eta$ denotes a viscosity of the fluid;
r denotes a radius of the charged particles.

Although the disclosure has been shown and described with respect to one or more implementations, equivalent alterations and/or modifications will occur to others skilled in the art based upon a reading and understanding of this specification and the annexed drawings. The disclosure includes all such modifications and alterations and is limited only by the scope of the following claims. In particular regard to the various functions performed by the above described components (assemblies, devices, circuits, etc.), the terms (including a reference to a "means") used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure. In addition, while a particular feature of the invention may have been disclosed with respect to only one of several implementations, such feature may be combined with one or more other features of the other implementations as may be desired and/or advantageous for any given or particular application. Furthermore, to the extent that the terms "includes", "having", "has", "with", or variants thereof are used in either the detailed description or the claims, such terms are intended to be inclusive in a manner similar to the term "comprising." Also, the term "exemplary" as utilized herein simply means an example, rather than the best.

What is claimed is:

1. A method for determining a fluid characteristic, comprising:
   flowing a fluid between first and second plates of a first electrode pair, the fluid containing charged particles when flowing between the first and second plates of the first electrode pair,
   flowing the fluid between first and second plates of a second electrode pair downstream of the first electrode pair, the fluid losing substantially all charged particles when flowing between the first and second plates of the second electrode pair;
   measuring a first current of the first electrode pair;
   measuring a second current of the second electrode pair; and
   determining the fluid characteristic based on one or more of the measured currents.

2. The method of claim 1 comprising:
   flowing the fluid between first and second plates of a third electrode pair with the second electrode pair disposed between the first and third electrode pair, substantially all of the charged particles having been removed from the fluid when the fluid flows between the first and second plates of the third electrode pair.

3. The method of claim 2 wherein determining the fluid characteristic comprises determining a DC conductivity from a current measured from the third electrode pair according to:

$$\sigma_{dc} = I_3/V_{Hi}*d/(L_3*D)$$

where
$I_3$ denotes the current measured between the first and second plates of the third electrode pair;
$V_{Hi}$ denotes a high voltage applied to third electrode pair;
$L_3$ denotes a length of third electrode pair in the direction of the flow;
D denotes a width of third electrode pair; and
d denotes a gap between the first and second plates of the third electrode pair.

4. The method of claim 1 comprising:
   adding charged particles to the fluid upstream of the first electrode pair.

5. The method of claim 1, the first plates of the respective electrode pairs comprising a common plate.

6. The method of claim 1, the first plates of the respective electrode pairs comprising a cylindrical drum, where rotation of the drum facilitates the flowing of the fluid.

7. The method of claim 1 comprising:
   applying respective DC voltages across at least one of the electrode pairs.

8. The method of claim 1, the fluid comprising a dielectric liquid media containing charged particles.

9. The method of claim 8, the second electrode pair having a length along the direction of fluid flow that is greater than a length of the first electrode pair along the direction of fluid flow.

10. The method of claim 1, the current between the plates of the electrode pairs flowing transverse to the direction of fluid flow.

11. The method of claim 1 further comprising:
    flowing the fluid between first and second plates of a third electrode pair, the third electrode pair being disposed downstream in a direction of the fluid flow from the first and second electrode pair, none of the first plates fully encircling the second plates and none of the second plates fully encircling the first plates.

12. The method of claim 11 wherein determining the fluid characteristic comprises determining a total charge of the fluid per unit volume from a current measured from respective first, second and third electrode pairs according to:

$$Q_V = (I_1 + I_2 - [L_1 + L_2]/L_3 * I_3)/(v*D*d)$$

where
$I_1$ denotes the current between the first and second plates of the first electrode pair;
$I_2$ denotes the current between the first and second plates of the second electrode pair;
$I_3$ denotes the current between the first and second plates of the third electrode pair;
$L_1$ denotes a length of the first electrode pair in the direction of the flow;

$L_2$ denotes a length of the second electrode pair in the direction of the flow;

$L_3$ denotes a length of third electrode pair in the direction of the flow;

D denotes a width of the respective first, second and third electrode pairs;

d denotes a gap between the first and second plates of the first, second and third electrode pairs; and v denotes a linear speed of the fluid flow.

13. The method of claim 1, the fluid containing charged particles being an electrophotography ink comprising a dispersion of the charged particles in a dielectric fluid.

14. The method of claim 1 wherein determining the fluid characteristic comprises determining a high field conductivity from the current measured from the first electrode pair according to:

$$\sigma_{Hi}=I_1/V_{Hi}*d/(L_1*D)$$

where $I_1$ denotes the current measured between the first and second plates of the first electrode pair, $V_{Hi}$ denotes a high voltage applied to the first electrode pair, $L_1$ denotes a length of the first electrode pair in the direction of the fluid flow, D denotes the width of the first electrode pair, and d denotes the gap between the first and second plates of the first electrode pair.

15. The method of claim 14 further comprising determining a particle conductivity from the current measured from the first electrode pair according to:

$$\sigma_{Part}=\sigma_{Hi}-\sigma_{Lo}$$

where $\sigma_{Hi}$ denotes the high field conductivity, $\sigma_{Lo}$ denotes the low field conductivity;

where $$\sigma_{Lo}=I_1/V_{Lo}*d/(L_1*D)$$

and where $V_{Lo}$ denotes a low voltage applied to first electrode pair.

16. The method of claim 15 further comprising determining a mobility of the charged particles according to:

$$\mu=\sigma_{Part}/Q_V$$

where $\sigma_{Part}$ denotes the particle conductivity;

$Q_V$ denotes total charge of the fluid per unit volume, being determined from a current measured from the respective first, second and third electrode pairs according to:

$$Q_V=(I_1+I_2-[L_1+L_2]/L_3*I_3)/(v*D*d)$$

where $I_1$ denotes the current between the first and second plates of the first electrode pair;

$I_2$ denotes the current between the first and second plates of the second electrode pair;

$I_3$ denotes the current between the first and second plates of the third electrode pair;

$L_1$ denotes a length of the first electrode pair in the direction of the flow;

$L_2$ denotes a length of the second electrode pair in the direction of the flow;

$L_3$ denotes a length of third electrode pair in the direction of the flow;

D denotes a width of the respective first, second and third electrode pairs;

d denotes a gap between the first and second plates of the first, second and third electrode pairs; and v denotes a linear speed of the fluid flow.

17. The method of claim 15 further comprising determining a volume concentration of the charged particles according to:

$$C_V=k*Q^2_V/\sigma_{Part}$$

where $\sigma_{Part}$ denotes the particle conductivity;

k is a proportionality factor that in the theoretical limits of uniform spherical particles can be calculated as:

$$k=1/(6*\pi*\eta*r)$$

where $\eta$ denotes a viscosity of the fluid;

r denotes a radius of the charged particles $Q_V$ denotes total charge of the fluid per unit volume, being determined from a current measured from the respective first, second and third electrode pairs according to:

$$Q_V=(I_1+I_2-[L_1+L_2]/L_3*I_3)/(v*D*d)$$

where $I_1$ denotes the current between the first and second plates of the first electrode pair;

$I_2$ denotes the current between the first and second plates of the second electrode pair;

$I_3$ denotes the current between the first and second plates of the third electrode pair;

$L_1$ denotes a length of the first electrode pair in the direction of the flow;

$L_2$ denotes a length of the second electrode pair in the direction of the flow;

$L_3$ denotes a length of third electrode pair in the direction of the flow;

D denotes a width of the respective first, second and third electrode pairs;

d denotes a gap between the first and second plates of the first, second and third electrode pairs; and v denotes a linear speed of the fluid flow.

18. The method of claim 1 wherein determining the fluid characteristic comprises determining a low field conductivity from the current measured from the first electrode pair according to:

$$\sigma_{Lo}=I_1/V_{Lo}*d/(L_1*D)$$

where $I_1$ denotes the current measured between the first and second plates of the first electrode pair;

$V_{Lo}$ denotes a low voltage applied to first electrode pair;

$L_1$ denotes a length of first electrode pair in the direction of the fluid flow;

D denotes a width of first electrode pair; and d denotes a gap between the first and second plates of the first electrode pair.

19. The method of claim 1, wherein the fluid is in contact with the first and second plates of at least the second electrode pair.

* * * * *